United States Patent [19]

Woods et al.

[11] 4,244,917
[45] Jan. 13, 1981

[54] SAMPLE PYROLYSIS OVEN

[75] Inventors: Roger A. Woods; Harry Dembicki, Jr., both of Ponca City, Okla.

[73] Assignee: Conoco, Inc., Ponca City, Okla.

[21] Appl. No.: 37,937

[22] Filed: May 9, 1979

[51] Int. Cl.³ .................... G01N 31/08; G01N 31/12
[52] U.S. Cl. ................................ 422/78; 23/230 PC; 23/232 C; 422/80; 422/89; 432/198
[58] Field of Search ............... 23/230 PC, 232 C; 422/78, 80, 93, 89; 432/58, 198, 200; 219/10.55, 10.69

[56] References Cited

U.S. PATENT DOCUMENTS

| | | |
|---|---|---|
| 2,634,360 | 4/1953 | Kusa .............................. 422/78 X |
| 3,235,336 | 2/1966 | Matsuyama et al. ............ 422/78 X |
| 3,647,385 | 3/1972 | Stephens ......................... 422/78 X |
| 3,726,646 | 4/1973 | Kravetz et al. ................... 422/78 |
| 4,066,411 | 1/1978 | Fine et al. ................... 23/230 PC X |

Primary Examiner—Michael S. Marcus
Attorney, Agent, or Firm—William J. Miller

[57] ABSTRACT

A pyrolysis oven for derivation of pyrolysis products from a selected sample which utilizes a tube within a tube structure of quartz glass for controlled sample heating preparatory to applying pyrolysis products for subsequent analysis. The apparatus includes a dual input helium supply to both the sample tube and oven tube with derived pyrolysis products delivered through a heated zone to the analyzing apparatus.

7 Claims, 2 Drawing Figures

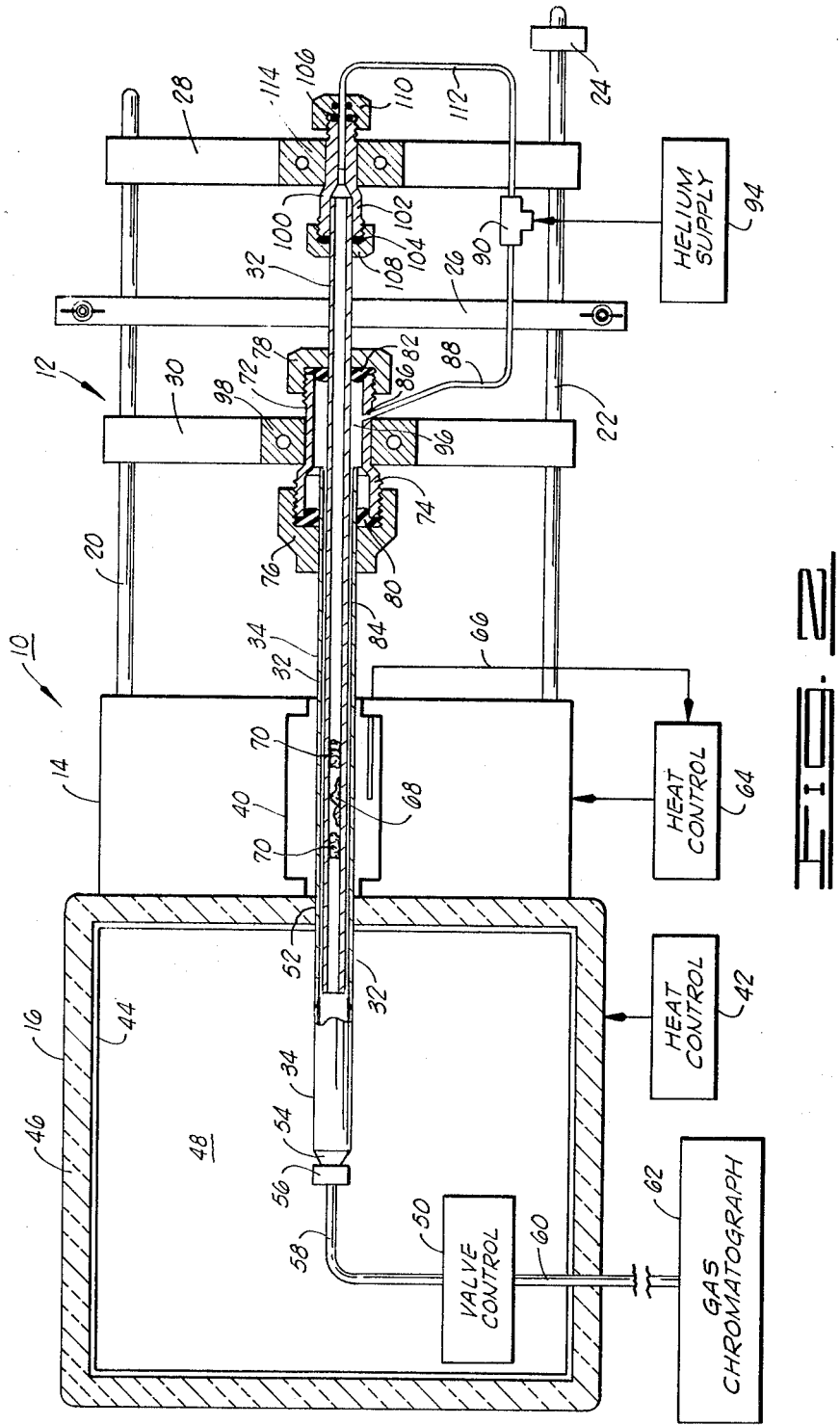

SAMPLE PYROLYSIS OVEN

BACKGROUND OF THE INVENTION

1. Field of the Invention

The invention relates generally to solid or liquid sample pyrolysis ovens and, more particularly, but not by way of limitation, it relates to an improved pyrolysis oven that employs glass tubing with a controlled heat furnace environment.

2. Description of the Prior Art

While there have in the past been numerous types of pyrolysis ovens utilizing various types of sample holding structures and product evacuation techniques, Applicant knows of no prior structure which utilizes concentric tube structure as set forth herein. Past approaches to tube furnace apparatus have necessitated the inclusion of a segment of gold or silver tube in order to maintain a proper heated zone for the pyrolysis breakdown.

SUMMARY OF THE INVENTION

The present invention contemplates a glass tube furnace designed to deliver pyrolysis products to a heated environment for subsequent analysis, e.g. delivery to a gas chromatograph. The invention imploys a quartz glass sample tube disposed concentrically within a quartz glass oven tube with such tubes extending from an external position through a heat-controlled oven to a constant heat zone. Helium is then flow-applied under pressure at the external position to both the sample tube and the annular space between the sample tube and oven tube, and pyrolysis products are recovered in the constant heat zone from the oven tube for conveyance to the analyzing instrument.

Therefore, it is an object of the present invention to provide a pyrolysis oven that eliminates conductance of heat from a constant heated zone back to the sample thus preventing sample preheating.

It is also an object of the invention to provide a pyrolysis oven which allows sample heating to be controlled solely by the furnace thereby enabling a greater degree of control.

It is yet another object of the present invention to provide a pyrolysis oven which eliminates back flow of pyrolysis products to the external cool ends of the oven and sample tubes.

Finally, it is an object of the invention to provide an improved form of pyrolysis oven which lessons the possiblity of sample contamination while prolonging the usable lifetime of sealing materials.

Other objects and advantages of the invention will be evident from the following detailed description when read in conjunction with the accompanying drawings which illustrate the invention.

BRIEF DESCRIPTION OF THE DRAWINGS

FIG. 2 is a top view shown in section (2—2 of FIG. 1), and including parts in block diagram, of the pyrolysis oven as shown in FIG. 1.

DETAILED DESCRIPTION OF THE INVENTION

Figure 1:
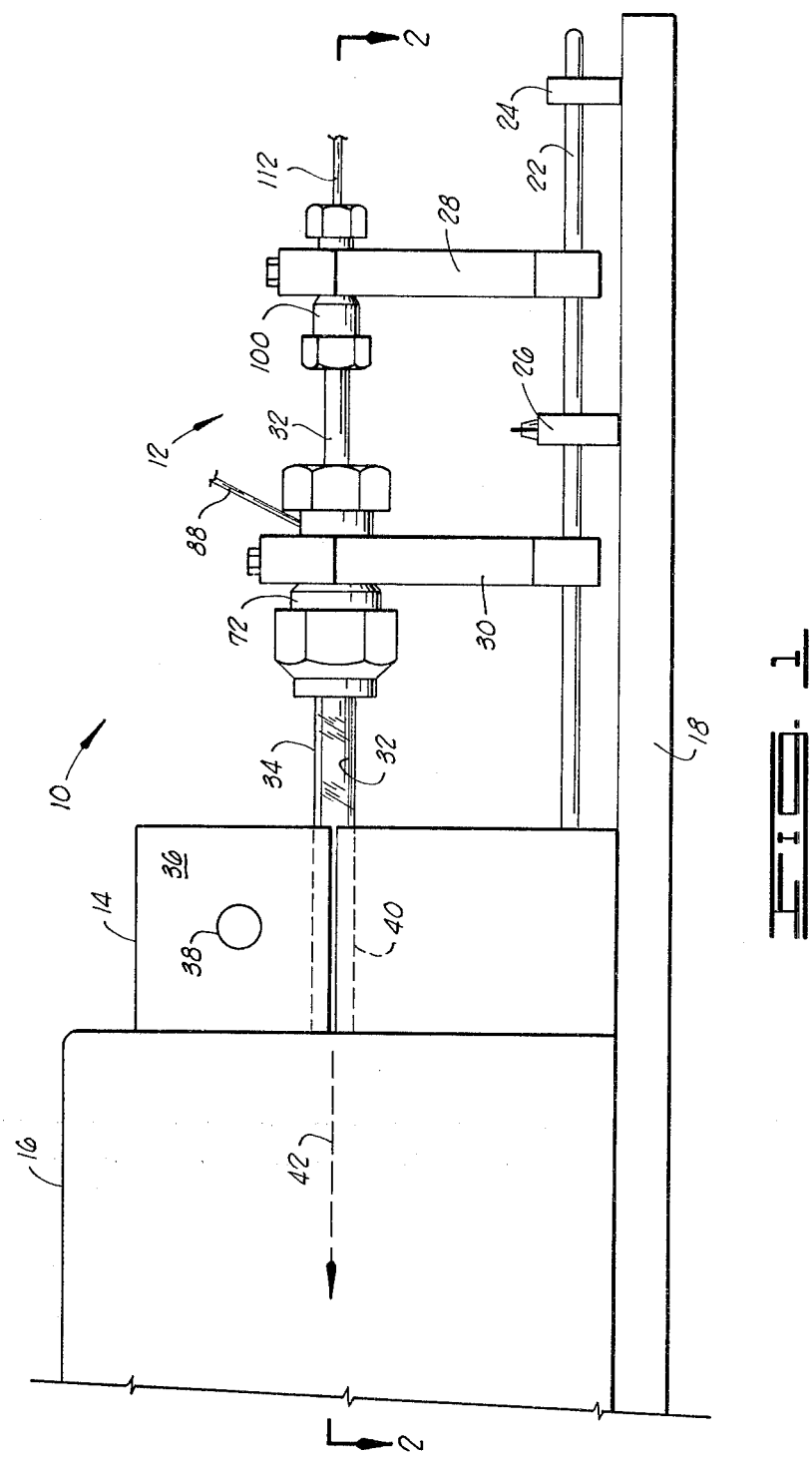
FIG. 1 is a partial front view in elevation showing a pyrolysis oven constructed in accordance with the present invention.

FIG. 1 illustrates a pyrolysis oven 10 consisting of a tubing support 12, a controlled heat furnace 14 and a constant heat oven 16. The entire assembly is rigidly secured to a suitable base 18 so that precise alignment of the interactive components can be maintained. A pair of guide rods 20 and 22 are rigidly secured in parallel as supported by blocks 24 and 26 affixed to base 18, and the inward ends of guide rods 24 and 26 are rigidly secured to the oven 14. The guide rods 20 and 22 are maintained in parallel in relation to each other and to the top of base 18 thereby to slidably support the glass tube oven assembly, as will be further described.

Adjustable bridges 28 and 30 are slidably retained on the guide rods 20 and 22 and serve to support a sample tube 32 and oven tube 34 in precise alignment, with sample tube 32 maintained concentric within oven tube 34 as both are inserted through the furnace bore of sample furnace 14 and into the interior heated enclosure of constant heat oven 16.

The sample furnace 14, having a hinged top 36, is manipulated by a handle 38 to expose a cylindrical sample furnace bore extending therethrough as shown by dash lines 40. In present design, the sample furnace used has a center bore 40 of 0.5 inches diameter as it receives a quartz glass oven tube of 9 millimeter outside diameter therethrough. The sample furnace 14 may be such as Model 34-2.5 available from Thermcraft, Inc. of Winston-Salem, N.C. Thus, sample furnace 14 is operated with a supply of 28.5 volts D-C to a maximum power requirement of 300 watts and maximum temperature of 800° Centigrade. The sample furnace 14 may be adjusted between 60° and 750° C., depending on the exigencies of pyrolysis testing, and the heated zone within oven 16 is maintained at a constant 300° Centigrade. The oven 16 may be any commercially available heat enclosure having a suitable heat control 42, i.e. heat source and thermostatic control.

Referring also to FIG. 2, the constant heat oven 16, including enclosure structure 44 and suitable insulation 46, preferably defines an internal volume enclosure 48 of size to accomodate selected valve control apparatus 50, not a subject of the present invention. Oven 16 is securely affixed contiguous to sample furnace 14 and a sealed bore 52 is provided to allow entry of the downstream end of oven tube 34. In present design, the oven tube 34 is 9 millimeter O.D. quartz glass tubing while the concentrically positioned sample tube 32 is 6 millimeter O.D. quartz glass tubing. Within the 300° C. constant heat zone 48 of oven 16, a graded glass seal 54, quartz to pyrex, is bonded to oven tube 34 and it is fitted with a covar seal 56 as further secured to a quarter-inch stainless steel tubing 58 for flow through valve control 50 and stainless tubing 60 to a gas chromatograph 62. In present design, a Hewlett-Packard Model 5730A Gas Chromatograph is utilized.

In sample furnace 14, the furnace bore 40 is maintained at a preselected heat by means of adjustable heat control 64 responsive to input from thermocouple 66. As illustrated, a selected pyrolysis sample 68, either liquid or solid, is placed in sample tube 32 and maintained therein by glass wool wadding 70 for proper placement in the central region of furnace bore 40.

The quartz glass tubes, thinner sample tube 32 and the enveloping oven tube 34, are maintained in precise positioning by the tubing support 12 and its attendant structure. A first bridge 30 is slidably mounted across guide rods 20 and 22 to support a modified SWAGLOK reducer fitting 72 in alignment with the furnace bore 40 and sealing entry 52 into oven 16. The fitting 74 with mating threaded retaining caps 76 and 78, respectively. Retaining cap 76, in conjunction with a sealing ring 80, maintains the oven tube 34 in rigid, precise alignment, while retaining cap 78 and seal 82 maintain the sample tube 32 in precise insertion within oven tube 34 to maintain a radially equal annulus along their contiguous length. The reducer fitting 72 is modified to include an orifice 86, a 1/16 inch hole, which receives a stainless steel tubing 88 in silver soldered affixure, from T-connector 90 and helium supply 94. The tubing 88 communicates with the union interior 96 and the annulus 84 within oven tube 34. A standard form of screw-fastened bracket 98 is used to maintain the union fitting 72 atop the bridge 30.

The outer end of sample tube 32 is supported in similar manner by a fitting 100 consisting of a threaded reducing union 102, seals 104 and 106, and retaining caps 108 and 110. The fitting 100 may be such as a standard SWAGLOK ¼ inch to 1/16 inch reducer union. The seal 104 and retaining cap 108 maintain sample tube 32 in precise annular insertion within oven tube 34, while a stainless steel tubing 112 from the helium supply T-connector 90 is connected by seal 106 and retainer cap 110. Here again, a standard form of screw-fastened bracket 114 may be utilized to secure the fitting 100 on the bridge 28.

In operation, and referring to FIGS. 1 and 2, sample 68 is inserted within sample tube 32 and maintained in proper position by glass wool waddings 70. Thereafter, the sample tube 32 and oven tube 34 are aligned precisely, both as to their centered or equi-annular relationship and the sample positioning relative to furnace bore 40, by means of the slidingly adjustable bridges 30 and 28 in support of the respective tubes.

Heat control 64 as regulated by thermocouple 60 is then adjusted to maintain the sample heat within furnace bore 40 at the selected temperature within a range of 60° to 750° Centigrade. Helium under selected pressure from helium supply 94 is flowed through tubes 88 and 112 to produce a constant helium flow through not only sample tube 32 but also the annulus 84 within oven tube 34. As pyrolysis progresses, the pyrolysis products are carried downstream by helium flow to the heated end of oven tube 34 within the 300° Centigrade heated zone 48, and the pyrolysis products are then led via tube 58 to valve control 50 for application by tube 60 to the gas chromatograph 62.

The valve control 50, while not being a subject of the present invention, serves to provide specific routing and trapping of the pyrolysis product output thereby to enable certain analysis procedures in gas chromatograph 62. The valve control 50 is maintained in heated zone 48 and allows operation for collection of all or part of the pyrolysis product of a given sample in one sample trap while pyrolysis product of another sample trap can be simultaneously flowed to the gas chromatograph 62 for analysis. The function allows the collection of pyrolysis product from a sample in two different parts. This may be desirable when the pyrolysis of the sample is carried out using a linearly increasing temperature in the pyrolysis furnace, or it can be utilized in effecting isothermal pyrolysis where products are collected over periods of time rather than temperature ranges. The dual trapping system effected by valve control 50 is the specific subject matter of application Ser. No. 037,938 entitled "Pyrolysis Product Gas Analysis Method and Apparatus" as filed concurrently herewith.

The foregoing discloses a novel form of pyrolysis sample oven wherein the use of a tube within a tube serves to eliminate the conductance of heat from the 300° heated zone back toward the area of the pyrolysis sample. This then prevents preheating of the sample and allows heating to be controlled solely by the controlled-heat furnace and furnace bore. The helium flow both over the sample and through the external annulus prevents backflow of pyrolysis products to the cool ends of the tube structure, and this also allows placement of seals outside of the heated zone thereby to reduce thermal stress and and decomposition which may cause pyrolysis product contamination.

Changes may be made in the combination and arrangement of elements as heretofore set forth in the specification and shown in the drawings; it being understood the changes being made in the embodiments disclosed without departing from the spirit and scope of the invention as defined in the following claims.

The embodiments of the invention in which an exclusive property or privilege is claimed are defined as follows:

1. A pyrolysis oven for deriving pyrolysis products from a selected sample, comprising:
   furnace means having temperature controllable at a preselected level;
   constant heat zone means disposed contiguous to said furnace means;
   first glass tubing means supported to extend from a first end external to the furnace means through said furnace means with the second end terminating in said constant heat zone means;
   second glass tubing means containing a sample supported to extend from a first end at a point upstream of said first end of said first glass tubing means through said first glass tubing means first end and concentrically through said first glass tubing means to terminate within a lesser extension into said constant heat zone means then said first glass tubing means;
   means for introducing inert gas under pressure to said second glass tubing means first end and to said first glass tubing means first end;
   conduit means associated with said constant heat zone means and sealingly connected to said first glass tubing means second end to deliver the sample pyrolysis products;
   first support means adjustably positionable in alignment with said furnace means to sealingly support said first and second glass tubing means; and
   second support means adjustably positionable in alignment with said furnace means and said first support means to sealingly support said second glass tubing means.

2. A pyrolysis oven as set forth in claim 1 wherein: said first and second glass tubing means are quartz.

3. A pyrolysis oven as set forth in claim 1 wherein: said inert gas is helium.

4. A pyrolysis oven as set forth in claim 1 wherein said furnace means comprises:
   heating and insulating means having a furnace bore adapted to envelop a generally central portion of said first glass tubing means in relatively close tolerance; and
   means continually sensing temperature proximate said first glass tubing means.

5. A pyrolysis oven as set forth in claim 1 wherein said constant heat zone means comprises:

an oven enclosure defining an internal constant heat volume and having a sealing orifice for receiving said first glass tubing means therein; and temperature control means for maintaining said volume at a selected temperature greater than ambient.

6. A pyrolysis oven as set forth in claim 1 wherein said first support means comprises:

a bridge support member; and a reducing union having first and second ends and being secured to said support member to receive sealingly said first tubing means at the first end and to receive sealingly said second tubing means through said second end, said reducing union including an orifice for receiving inert gas for annular entry between said first and second tubing means.

7. A pyrolysis oven as set forth in claim 1 wherein said second support means comprises:

a bridge support member; and a reducing union having first and second ends and being secured to said support member to receive sealingly said second tubing means at the first end and to receive sealingly an inert gas conduit at said second end.

* * * * *